United States Patent [19]
Hecht et al.

[11] Patent Number: 6,075,057
[45] Date of Patent: *Jun. 13, 2000

[54] INHIBITION OF CARBOHYDRATES METABOLISM BY QUINONE COMPOUNDS

[75] Inventors: Sidney M. Hecht; Edward Locke, both of Charlottesville, Va.

[73] Assignee: The University of Virginia Patent Foundation, Charlottesville, Va.

[*] Notice: This patent issued on a continued prosecution application filed under 37 CFR 1.53(d), and is subject to the twenty year patent term provisions of 35 U.S.C. 154(a)(2).

[21] Appl. No.: 08/831,744

[22] Filed: Apr. 1, 1997

Related U.S. Application Data
[60] Provisional application No. 60/014,682, Apr. 1, 1996.

[51] Int. Cl.[7] .................. A61K 31/12; A61K 31/05; C07C 49/105; C07C 39/12
[52] U.S. Cl. .................. 514/682; 514/679; 514/731; 514/732; 568/325; 568/328; 568/731; 568/734
[58] Field of Search .................. 568/325, 328, 568/731, 734; 514/682, 732, 731, 679

[56] References Cited

U.S. PATENT DOCUMENTS

| | | | |
|---|---|---|---|
| 4,939,177 | 7/1990 | Muller | 514/729 |
| 4,946,869 | 8/1990 | Muller et al. | 514/729 |
| 5,026,732 | 6/1991 | Muller | 514/691 |
| 5,204,367 | 4/1993 | Wright et al. | 514/453 |

*Primary Examiner*—Deborah C. Lambkin
*Attorney, Agent, or Firm*—Oblon, Spivak, McClelland, Maier & Neustadt, P.C.

[57] ABSTRACT

Optically pure enantiomers of avarol are obtained. The enantiomers of avarol are demonstrated to be highly effective inhibitors of α-glucosidase and α-mannosidase. Other enzymes assayed were not inhibited by these optically pure compounds. Inhibition of these two enzymes is useful for a variety of assays and probes, and offers particular utility in the treatment of retroviral infection-associated syndromes, such as AIDS.

18 Claims, 10 Drawing Sheets

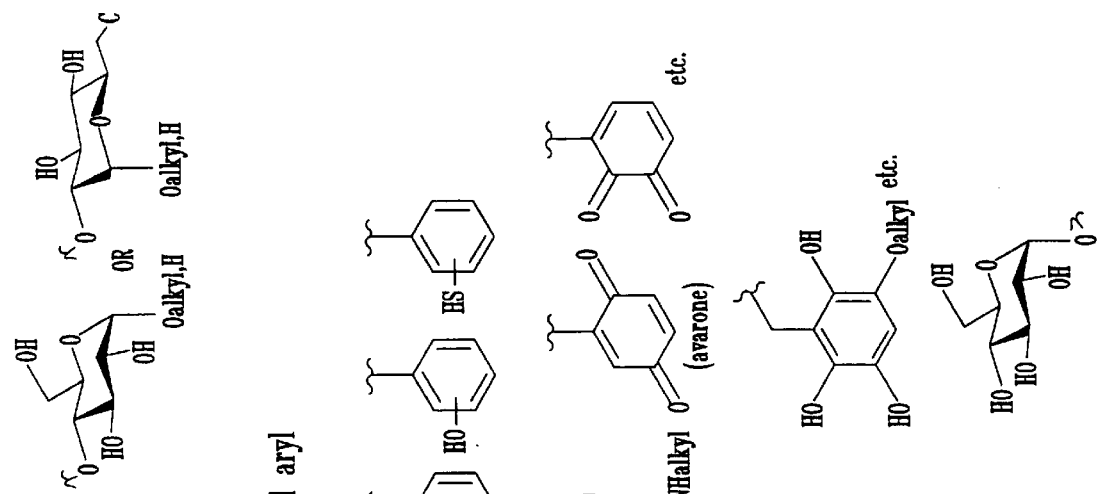
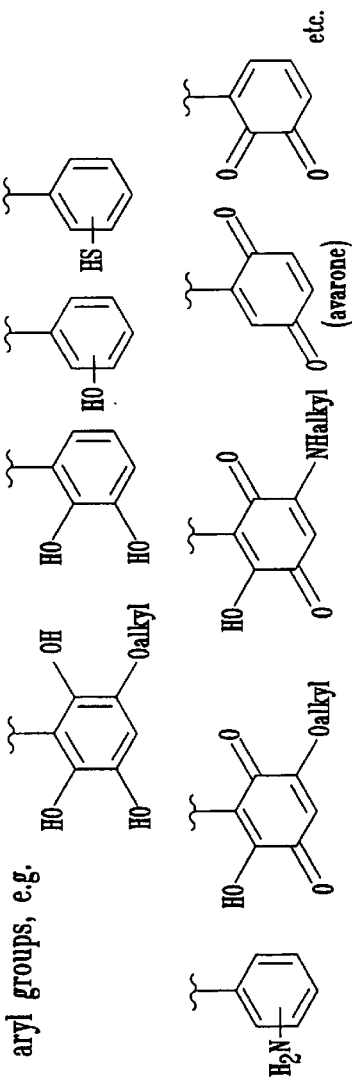

X=C,O,N,S
Y=C,O,N,S $R_1$=H, lower alkyl, $CO_2$alkyl, CHO, $NO_2$, CN, ═X
$R_2$=H,I,Br,Cl,F,lower alkyl, $CO_2$alkyl, ═X
$R_3$=H,OH,$NH_2$, SH, substituted aryl,
$R_4$=H,OH,$NH_2$, SH, substituted aryl
$R_5$=H, lower alkyl, $CH_2$OH, $CH_2NH$, $CH_2SH$, substituted aryl
$R_6$=H, lower alkyl, OH, $NH_2$, SH, various substituted aryl groups, e.g.

or one carbon homologated versions of these, e.g.

$R_7$=H, lower alkyl, OH, $NH_2$, SH
$R_8$=H, lower alkyl, substituted aryl, OH, $NH_2$, SH,
$R_9$=H, OH, $NH_2$, SH, substituted aryl,
$R_{10}$=H, lower alkyl, $CH_2$OH, $CH_2NH_2$, $CH_2SH$

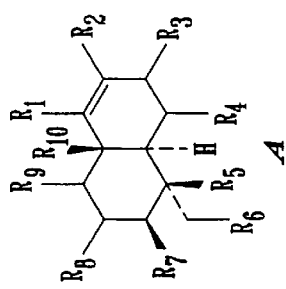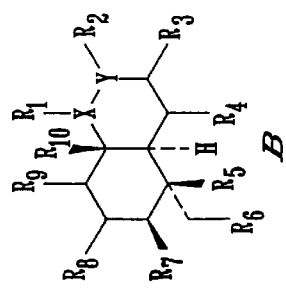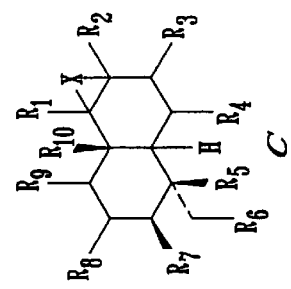

FIG. 12

NATURAL
(+)-AVAROL
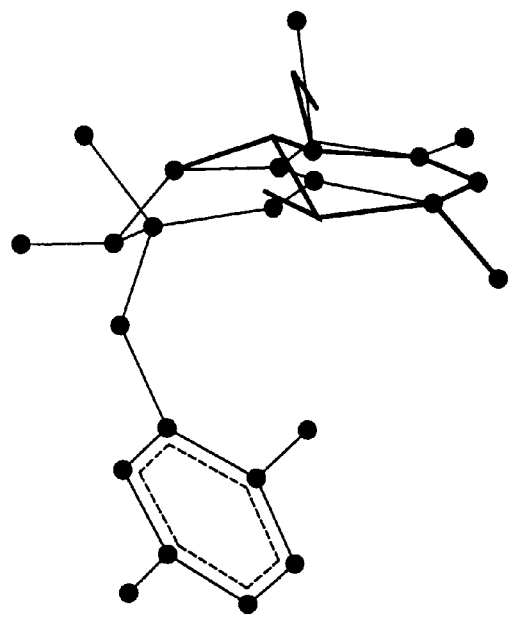
(−)-AVAROL
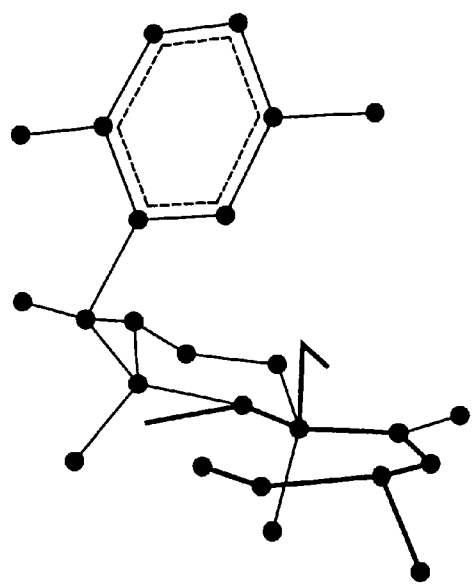
*FIG. 13*

INHIBITION OF CARBOHYDRATES METABOLISM BY QUINONE COMPOUNDS

This application is a regular National application claiming priority from Provisional Application, U.S. Application Ser. No. 60/014,682 filed Apr. 1, 1996. The United States Government may have rights to this application pursuant to NIH Contract CA53913.

BACKGROUND OF THE INVENTION

1. Field of the Invention

This invention pertains to the identification of methods for inhibiting α-glucosidase and α-mannosidase, as well as the identification of optically pure enatiomers which inhibit these enzymes. Specifically, a family of compounds, which includes the two enantiomers of avarol, including the natural (+)-avarol and the non-natural (−)-avarol, synthetically prepared, and derivatives are demonstrated to be potent, selective inhibitors of these important enzymes.

2. Introduction

The toxicity of quinones is well-documented[1] and explains the mutagenicity and carcinogenicity of many aromatic organic compounds existing as natural products, synthetic medicines, and environmental pollutants. Through metabolic processes these compounds are converted to quinonoid species responsible for their toxic effects. Quinones are widely used as bactericides, fungicides, and clinically useful chemotherapeutic agents possessing antileukemic and antitumor activity. Studies conducted with simple achiral quinones (e.g. p-benzoquinone, chloranil) have suggested that their toxic activity can be attributed not only to their ability to undergo redox cycling but also to their potential binding and alkylation of nucleic acids and essential thiol and amino groups in proteins[1]. The former process involves the production of the malign species superoxide radical, hydrogen peroxide, and hydroxyl radical which are believed to cause oxidative stress in cells by damage inflicted on DNA. The latter reflects the electrophilic nature of the quinone moiety. Given the facile conversion of hydroquinones to quinones under aerobic conditions,[2] it stands to reason that chiral substituents on a hydroquinone nucleus might impart a degree of selectivity to the interaction between the respective quinone and asymmetric cellular components such as nucleic acids and highly organized proteins.

Glycosyl hydrolases[3] (glycosidases) are an important class of enzymes that catalyze the hydrolysis of glycosidic bonds in polysaccharides and glycoproteins. The generally-accepted mechanism[4] for this hydrolysis is where general acid-base catalysis by key residues in the protein serves to effect the transformation. The glycosidases can be grouped into two broad classes depending on whether the hydrolysis reaction they catalyze leads to overall retention or inversion at the anomeric center of the hydrolysis site. Both cases involve direct participation of a nucleophile and a proton donor positioned on opposite sides of the bond to be hydrolyzed. With inverting glycosidases, the difference involves a larger separation between these catalytic residues (~5.5 angstroms for retaining enzymes vs. ~9.5 angstroms for inverting enzymes) to accommodate a water molecule.[5]

Given the importance of polysaccharides and glycoproteins in cell-cell and host-pathogene recognition and their implication in the control of biological events,[6,7,8] the relevance of the potentiation of their synthesis and/or function has grown tremendously. The ability to inhibit the biosynthetic pathways to carbohydrates and carbohydrate-protein conjugates is significant in the study of cellular and extracellular events and in the development of antiviral,[6] antidiabetic,[7] and antitumor[8] chemotherapeutic strategies. At least two α-glucosidase inhibitors are currently in clinical trials for treatment of HIV-associated AIDS.

The quest for therapeutic strategies against the human immunodeficiency virus (HIV) and its ultimate manifestation, AIDS, represents a monumental effort in contemporary medicine and chemistry. To date, more than a half-million people in America alone have contracted the AIDS virus and the number continues to grow at an alarming rate. Several FDA-approved drugs are now being used clinically in various combinations or "cocktails" to ward off the virus and its detrimental consequences. All the currently approved drugs target one of two key retroviral enzymes, reverse transcriptase or protease, which are essential for replication and survival of the virus.

Another promising strategy indirectly targets the initial association and recognition event between the HIV virus and the fated host cell. The CD4 surface protein has been shown to be a specific cellular receptor for HIV. Klatzman et al., Nature 310:767 (1984) and Dalgleish et al., Nature 310:763 (1984). The CD4 antigen is bound by the envelope glycoprotein gp 120, a heavily glycosylated surface protein expressed by HIV, in the virus-host cell association event leading to cell membrane fusion and infectivity. The successful synthesis of a functional gp 120 can be hampered by inhibiting glycohydrolase enzymes (glycosidases) that act as the protein tailors of the cell. These enzymes are responsible for the selective trimming of carbohydrate moieties from the glycosylated protein as it is synthesized within the cell. The inhibition of certain glycosidases has been shown to have a profound effect on both the cell surface expression and function and topology of glycoproteins. Nichols et al., Mol. Cell. Biol. 5:3467 (1985). Thus, inhibitors of certain glycosidases, namely those which have an impact on the production of a competent gp120 glycoprotein, are potential candidates for the therapeutic treatment of HIV infection.

Since its isolation in 1974 from the marine sponge *Dysidea avara* by Minale et al.[10] avarol has been the subject of numerous biological studies seeking a better understanding of how this compound and its corresponding quinone exhibit their potent biological effects:

- in vitro and in vivo inhibition of microtubule polymerization[11]
- highly selective cytotoxicity against L5178Y mouse lymphoma cells in vitro and in vivo[2a]
- in vitro inhibition of replication[12] of HTLV-III/LAV (the etiologic agent of AIDS)

Additionally, both avarol and avarone have been shown to be neither direct nor indirect mutagens[13] n the Ames-microsomal assay[14] and possess antimutagenic activity through the inhibition of benzo[a]pyrene monooxygenase.[13] Thus, an interesting scenario is presented in which avarol and avarone combine potent cytotoxicity and antiviral properties with antimutagenic activity.

Accordingly, it remains an object of those of skill in the art to obtain potent, preferably selective, inhibitors of glycosyl hydrolases. It is a further desire to elucidate the mechanism of action of avarol and avarone.

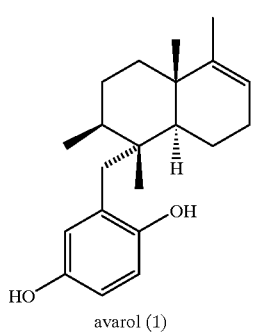
avarol (1)
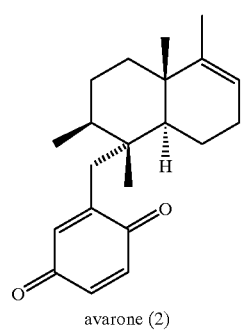
avarone (2)
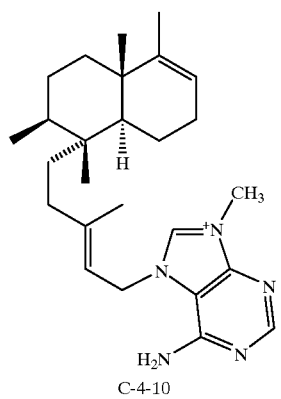
C-4-10
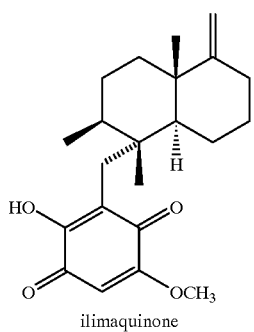
ilimaquinone
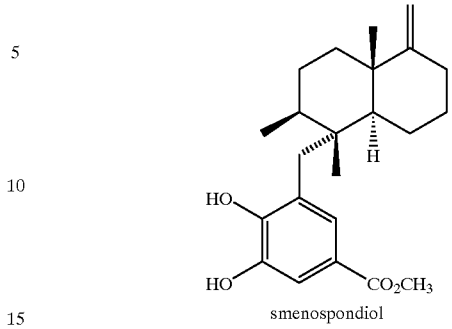
smenospondiol
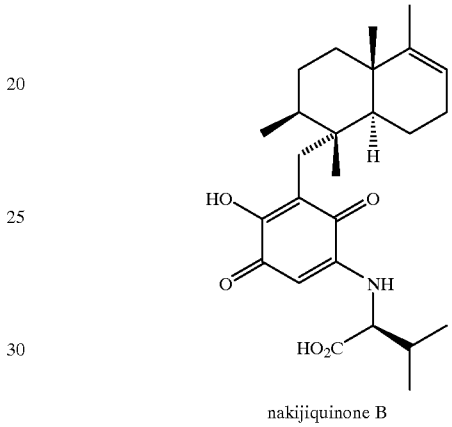
nakijiquinone B
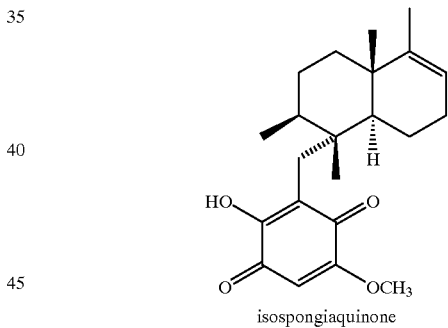
isospongiaquinone
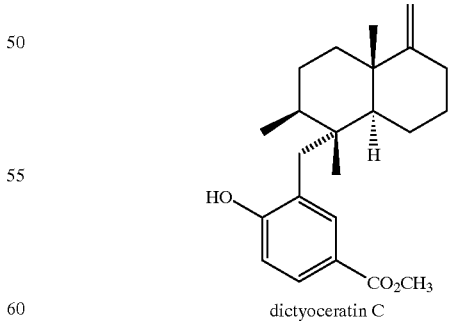
dictyoceratin C -continued

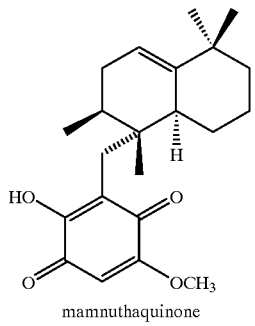

mamnuthaquinone

SUMMARY OF INVENTION

Optically pure enantiomers of avarol were synthetically prepared. A survey of potential inhibitory activity by avarol against twelve glycosidases was performed according to general procedures[15] (see experimental section). The two enantiomers of avarol prove to be extremely selective, potent inhibitors of α-glucosidase and α-mannosidase. Of particular interest is the fact that the non-natural isomer (−)-avarol was significantly more active as an inhibitor than the naturally-occurring (+)-avarol with respect to both inhibited enzymes. These enantiomers offer promise as particularly potent inhibitors, having utilities both as probe and assay components, and as drugs, particularly potential combinatorial drugs, in the treatment of AIDS and related retroviral-induced syndromes, particularly desirable because of their high selectivity.

BRIEF DESCRIPTION OF THE FIGURES

FIG. 12 sets forth the proposed structural formulae of inhibitory compounds within the scope of this invention.

FIGS. 13A and B are computer assisted molecular models of natural (+) and nonnatural (−) avoral overlayed with the α-glucose oxonium ion.

DETAILED DESCRIPTION OF THE INVENTION

Synthesis of Optically Pure Enantiomers

Figure 1:
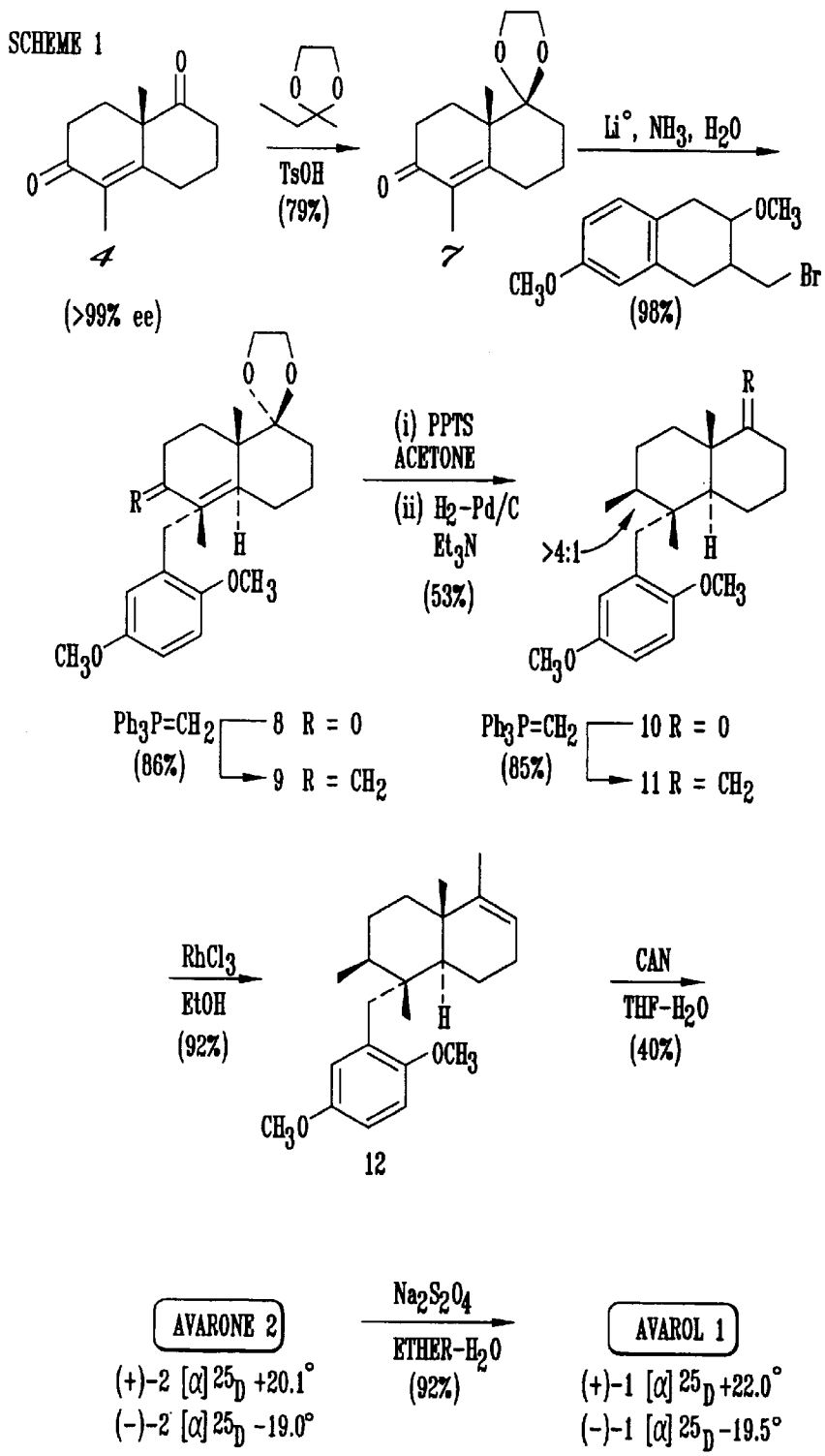
FIG. 1 is a schematic representation of the synthetic scheme for obtaining the optically pure compounds of this invention.

The synthesis scheme for production of optically pure enantiomers of avarol is set forth in FIG. 1. After experiencing several unsuccessful attempts at the final conversion in the synthetic sequence to avarol, a less direct strategy was devised that proved very practical and effective. Using the versatile ceric ammonium nitrate (CAN), oxidative removal of the methyl protecting groups with concomitant oxidation provided avarone 2 as a yellow oil in 30–40% yield for each enantiomer. Subsequent treatment of the quinones with sodium dithionite in ether/water cleanly provided both natural and unnatural avarol 1 as almost colorless needles in 86–92% yield after chromatographic purification. The overall two-step transformation provided the desired antipodes in 32–37% yield. The somewhat low yield is offset by the ease and speed of the conversion which can be accomplished in a day's work. The two enantiomers were isolated and recovered in essentially optically pure focus. The optical rotation value for the optically pure (+) natural product, given below, is quite a bit higher than that given for reports of the natural product in the art, showing the natural form to be racemized to some degree.

General Methods. Elemental analyses were carried out by Supersun Technology Analytical Laboratory. Melting points were taken on a Thomas-Hoover or Fisher-Johns apparatus and are uncorrected. Optical rotation data were obtained on a Perkin Elmer 141 polarimeter. $^1$H NMR and $^{13}$C NMR spectra were recorded on a General Electric QE-300 MHz spectrometer with chemical shift values referenced to $CHCl_3$ at 7.26 ppm. Chemical ionization mass spectra were recorded on a Varian MAT-44 using methane (CI). High resulution mass spectra were determined at the Midwest Center for Mass Spectrometry, University of Nebraska, Lincoln. All reagents were purchased from Aldrich Chemical Co. or Lancaster Synthesis and were used as received unless otherwise noted. All solvents were analytical reagent grade. Tetrahydrofuran was distilled from sodium/benzophenone. Dichloromethane and benzene were distilled from calcium hydride. Triethylamine was distilled from and stored over potassium hydroxide. All moisture-sensitive reagents were desiccated over anhydrous calcium chloride or phosphorous pentoxide and transferred under an argon atmosphere. All reactions were performed under an inert atmosphere of argon and analyzed by TLC on E. Merck silica gel $F_{254}$ glass-backed plates. Silica gel flash chromatography was performed as described, Kahn et al., J. Org. Chem. 43:2923 (1978) on silica gel 60 (35–75 μm).

Refer to the following general numbering scheme for the $^1$H NMR assignments of the decalin systems described.

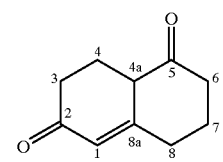

(+)-1,4aβ-Dimethyl-5β-hydroxy4,4a,5,6,7,8-hexahydronaphthalen-2(3H)-one (5). Dutcher et al., J. Org. Chem. 41:2663 (1976). A solution of sodium borohydride (3.2 mg, 0.084 mmol, 1.1 eq) in 1.0 nL of absolute ethanol was added dropwise over 15 min to a cooled (0° C.) solution of (+)-4, Agami et al., Tetrahedron, 40:1031 (1976), see also, Uma et al., Tetrahedron Letters 25:5825 (1984) and Hagiware et al., J. Org. Chem. 53:2308 (1988), (59.0 mg, 0.306 mmol) in 0.5 mL of absolute ethanol under Ar. After stirring for an additional 10 min, the residual hydride was quenched by the addition of 5 drops of glacial acetic acid. The solvent was concentrated and the residue was dissolved in 10 mL of $CHCl_3$ and washed with 5 mL of distilled $H_2O$. The $CHCl_3$ layer was dried ($MgSO_4$) and concentrated to afford a clear, almost colorless oil which was purified by flash chromatography on a silica gel column (10×2 cm); elution with 35% EtOAc in hexanes provided (+)-5 as a colorless oil which slowly solidified under vacuum; yield 40 mg (67%); $[\alpha]^{25}_D$ +171.80° (c 1.21, CHCl₃), lit²[α]²⁵_D+162.6° (c 2.17, CHCl₃); mp 42–44° C.; silica gel TLC R_f 0.39 (1:1 EtOAc-hexanes); ¹H NMR (CDCl₃) δ 1.17 (s, 3H), 1.27–1.45 (qt. 1H, J=4, 13.5 Hz), 1.76 (d, 3H, J=1 Hz), 1.62–1.95 (m, 3H), 1.95–2.17 (m, 3H), 2.40–2.45 (m, 2H), 2.64–2.70 (m, 1H) and 3.83–3.43 (dd, 1H, J=4.5, 11.5 Hz); mass spectrum (chemical ionization), m/z 195 (M+1)⁺ and 177 (M–OH)⁺.

(+)-1,4aβ-Dimethyl-5β-hydroxy-4,4a,5,6,7,8-hyxahydronaphthalen-2(3H)-one α-Methoxy-α-trifluoromethylphenylacetate (6). Dutcher, supra. A solution of (+)-5 (12.0 mg, 0.06 mmol), R-(+)-α-trifluoromethylphenylacetic acid (42 mg, 0.18 mmol) and N,N-dimethylaminopyridine (5 mg) in 1.5 mL of CH₂Cl₂ was treated with 37 mg (0.18 mmol) of N,N'-dicyclohexylcarbodiimide at room temperature. After 19 h, the reaction mixture was applied directly to a preparative silica gel TLC plate, which was developed using 40% EtOAc in hexanes to provide (+)-6 as colorless microcrystals; yield 16 mg (64%); [α]²⁵_D +110.3° (c 0.33, CH₂Cl₂); mp 85–86° C.; silica gel TLC R_f 0.74 (1:1 EtOAc-hexanes); ¹H NMR (CDCl₃) δ 1.20 (s, 3H), 1.39–1.57 (qt. 1H, J=4, 13 Hz), 1.78 (d, 3H, J=1 Hz), 1.65–2.17 (m, 6H), 2.37 (dt, 2H), 2.73 (m, 1H), 3.56 (d, 3H J=1 Hz), 4.81–4.87 (dd, 1H, J=4.5, 11.5 Hz), 7.42 (m, 3H) and 7.53 (m, 2H); (±-6: ¹H NMR (CDCl₃)(s, 1.5H), 1.20 (s, 1.5H), 1.37–1.58 (m 1H), 1.79 (br s, 3H), 1.65–2.17 (m, 6H), 2.37–2.45 (m, 2H), 2.73 (m, 1H), 3.50 (s, 3H), 3.56 (s, 3H), 4.79 (dd, 0.5H J=4.5, 11.5 Hz), 4.84 (dd, 0.5H, J=4.5, 11.5 Hz) 7.38–7.47 (m, 3H) and 7.48–7.57 (m, 2H).

S-(+)-1,4aβ-Dimethyl-5,5-ethylenedioxy-4, 4a,7,8-tetrahydronaphthalen-2-(3H,6H)-one (7). McMurry, J. Am. Chem. Soc. 101:330 (1979). Ketone 4 (1.40 g 7.28 mmol) was dissolved in 2-ethyl-2-methyl-1,3-dioxolane (5.46 mL, 43.7 mol) containing a catalytic amount of anhydrous ethylene glycol (115 µL, 128 mg, 2.0 mmol). To the stirred solution was added 26 mg (0.14 mmol) of p-TsOH and stirring was continued at ambient temperature. After 42 h, 0.5 mL of Et₃N and 25 mL of benzene were added sequentially and the resulting solution was washed with 10 mL of H₂O and dried (MgSO₄). Concentration under diminished pressure gave a residue which was purified by flash chromatography on a silica gel column (13×4.5 cm); elution with 30% EtOAc in hexanes gave 7 as colorless crystals: yield 1.36 g (79%); [α]²⁵_D+125.8° (c 1.19, CH₂Cl₂); mp 57–58° C., lit⁴ mp 57–59° C.; silica gel TLC P_f 0.71 (1:1 EtOAc-hexanes); ¹H NMR (CDCl₃) δ 1.33 (s, 3H), 1.60–1.73 (m, 3H), 1.78 (d, 3H, J=1 Hz), 1.80–2.77 (m, 7H) and 3.96 (m, 4H); mass spectrum (chemical ionization, m/z 237 (M+1)⁺.

(+)-(1S,4aS,8aS)-1β,4aβ-Dimethyl-1α-[2',5'-dimethoxyphenyl)methyl]-5,5-ethylenedioxy-1,4,4a,5,6,7,8,8aα-octahydronaphthalen-2(3H)-one (8). Ammonia (60 mL) was distilled from lithium metal into a three-necked flask fitted wtih a dry ice condenser, glass stopper and rubber septum. Li° wire (305 mg, 44.0 mmol) was added and the solution was maintained at reflux for 30 min. A solution of ketone 6 (1.30 g, 5.50 mmol) in 30 mL of THF containing 99 µL (5.5 mmol) of H₂O was added dropwise to the ammonia solution at reflux. After 1 h, the reaction was quenched by rapid addition of a solution of 6.40 g (27.8 mmol) of 2,5-dimethoxybenzyl bromide in 14 mL of THF. The ammonia was allowed to evaporate overnight and the resulting residue was dissolved in 100 mL of CH₂Cl₂, washed with saturated aqueous NaHCO₃, then saturated brine, and dried (MgSO₄). Concentration under diminished pressure gave an oil solid which was purified on a silica gel column (17×5 cm); elution with 15% EtOAc in hexanes provided 8 as a clear, colorless syrup; yield 2.10 g (98%); [α]²⁵_D+23.80° (c 1.17, CH₂Cl₂); silica gel TLC R_f 0.66 (1:1 EtOAc-hexanes); ¹H NMR (CDCl₃) δ 1.02 (s, 6H), 1.30–1.91 (m, 8H), 2.20–2.36 (m, 2H), 2.42–2.56 (m, 1H), 2.76–2.90 (dd, 2H, J=13.5, 16 Hz), 3.68 (d, 3H, J=1 Hz), 3.71 (d, 3H, J=1 Hz), 3.79–4.0 (m, 4H), 6.58 (s, 1H) and 6.70 (s, 1H) and 6.70 (s, 2H); ¹³C NMR (CDCl₃) δ 17.66, 21.33, 23.16, 23.24, 28.82, 30.41, 35.66, 40.05, 42.53, 45.51, 52.23, 55.80, 56.13, 65.13, 63.45, 111.31, 112.81, 113.23, 118.25, 127.84, 152.78, 153.37 and 217.47; mass spectrum (chemical ionization) m/z 388 (M+1)⁺ and 237; mass spectrum (electron impact), m/z 3.88.225 (M⁺) (C₂₃H₃₂O₅ requires 388.225).

(+)-(1S, 4aS,8aS)-1β,4aβ-Dimethyl-1αa-[(2',5'-dimethoxyphenyl)methyl)-5,5-ethylenedioxy-2-exo-methylene-(3H)-1,4,4a,5,6,7,8,8aα-octahydronaphthalene (9). To a stirred suspension of 1.34 g (11.9 mmol) of anhydrous 95% potassium tert.-butoxide in 35 mL of benzene was added 4.05 g (11.35 mmol) of methyltriphenylphosphonium bromide; the resulting bright yellow solution was heated to reflux for 30 min. A solution of ketone 8 (2.10 g, 5.40 mmol) in 15 mL of benzene was added dropwise to the heated solution of the ylide. After 40 h heating at reflux, the reaction mixture was cooled and diluted sequentially with ether (100 mL) and H₂O (30 mL) with rapid stirring. The layers were separated and the organic phase was washed with 20 mL of H₂O and 30 mL of saturated brine, and then dried (MgSO₄). Concentration under diminished pressure gave a tan oil, which was purified by chromatography on a silica gel column (15×6 cm); elution with 10% EtOAc in hexanes gave 9 as a clear, colorless syrup: yield 1.79 g (86%); [α]²⁵_D+122.7° (c 0.72, CH₂Cl₂); silica gel TLC R_f 0.57 (20% EtOAc in hexanes); ¹H NMR (CDCl₃) δ 0.91 (s, 3H), 1.05 (s, 3H), 1.12–1.25 (m, 1H), 1.39–1.72 (m, 6H), 1.95–2.17 (m, 3H), 2.26–2.35 (m, 1H), 2.56–2.61 (d, 1H, J=13 Hz), 2.74–2.79 (d, 1H 3.70 (s, 3H), 3.73 (s, 3H), 3.88–4.03 (m, 4H), 4.27 (s, 1H), 4.74 (s, 1H) and 6.59–6.61 (m, 1H), 6.65–6.73 (m, 2H); ¹³C NMR (CDCl₃) δ 20.60, 21.29, 23.34, 23.43, 29.98, 30.16, 32.48, 40.25, 43.31, 43.91, 46.79, 56.04, 56.12, 64.90, 65.32, 107.85, 111.06, 111.84, 114.11, 119.48, 128.88, 152.79, 153.31 and 154.27; mass spectrum (chemical ionization), m/z 387 (M+1)⁺; mass spectrum (electron impact), m/z 386.246 (M⁺)(C₂₄H₃₄O₄ requires 386.246). Anal, Calcd for C34H34O₄: C, 74.58; H, 8.87. Found: C, 73.99; H, 9.03.

Deprotection of 9. Dioxolane 9 (1.75 g, 4.53 mmol) was dissolved in 100 mL of acetone containing 10 drops of H₂O, the resulting solution was treated with pyridinium p-toluenesulfonate (341 mg, 1.36 mmol) and heated to reflux. After 24 h of heating, the reaction mixture was cooled and concentrated to afford a residue. The residue was dissolved in 100 mL of CH₂Cl₂ and washed sequentially with 50 mL of saturated aqueous NaHCO₃ and 50 mL of saturated brine, and then dried (MgSO₄). Concentration under diminished pressure gave a clear oil which was purified on a silica gel column (17×6 cm); elution with 10% EtOAc in hexanes gave (+)-(1S,4aS,8aS)-1β,4aβ-dimethyl-1α-[(2',5'-dimethoxyphenyl)methyl]-2-exo-methylene-1,4, 4a,5,6,7,8,8aα-octahydronaphthalen-5-5(3H)-one as colorless microcrystals: yield 1.36 g (88%); [α]²⁵_D +151.7° (c 0.82, CH₂Cl₂); mp 94–95.5° C.; silica gel TLC R_f 0.59 (30% EtOAc in hexanes), 0.47 (20% EtOAc in hexanes); ¹H NMR (CDCl₃) δ 1.08 (s, 3H), 1.14 (s, 3H), 1.30–1.55 (m, 3H), 1.67–1.90 (m, 4H), 1.98–2.10 (m, 1H), 2.18–2.40 (m, 4H) 2.52 (dt, 1H, J=6.5, 14.5 Hz), 2.70 (s, 2H), 3.71 (s, 3H), 3.73 (s, 3H), 4.51 (d, 1H, J=1 Hz), 4.84 (s, 1H) and 6.63–6.74 (m, 3H); mass spectrumm (chemical ionization), m/z 343 (M+1)⁺. Anal, Calcd for C₂₂H₃₀O₃: C, 77.16; H, 8.83. Found: C, 77.18; H, 9.00.

(−)-(1R, 4aS,8aS)-1β,2β,4aβ-Trimethyl-1α[(2',5'-dimethoyphenyl)methyl]-1,2,3,4,4a,5,6,7,8,8aα-decahydronaphthalen-5-one (10). The ketone obtained from the hydrolysis of 9 (0.50 g, 1.46 mmol) was dissolved in 29 mL of dry Et$_3$N containing 15 drops of MeOH. To this solution was added 1.25 g of 10% Pd on carbon. The flask was flushed with H$_2$ and then stirred under one atmosphere of H$_2$ at 35° C. After 48 h, the heterogeneous reaction mixture was diluted with 60 mL of CH$_2$Cl$_2$ and the catalyst was removed by filtration through a Celite pad. The filtrate was washed with an additional portion of CH$_2$Cl$_2$ (15 mL) and the combined filtrate was concentrated to afford a residue which was purified by chromatography on a silica gel column (12×4 cm). Elution with 10% EtOAc in hexanes provided 10 as colorless needles from ether-petroleum ether): yield 304 mg (60%); [α]$^{25}_D$ −43.80° (c 0.34, CH$_2$Cl$_2$); mp 104–106° C., lit$^5$ mp((±)-10) 123° C.; silica gel TLC R$_f$ 0.32 (15% EtOAc-hexanes); $^1$H NMR (CDCl$_3$) δ 0.91 (s, 3H), 0.99–1.01 (d, 3H, J=5.5 Hz), 1.14 (s, 3H), 1.10–1.83 (m, 9H), 2.20–2.27 (m, 3H), 2.55–2.75 (AB q, 2H, J=14 Hz), 3.70 (s, 3H) 3.73 (s, 3H) and 6.60–6.75 (m, 3H); $^{13}$C NMR (CDCl$_3$) δ 17.78, 18.46, 19.39, 22.42, 26.09, 27.24, 32.77, 36.07, 37.64, 37.96, 42.79, 48.08, 49.74, 55.84, 55.99, 111.28, 111.49, 119.51, 128.41, 153.11, 153.20 and 216.70; mass spectrum (chemical ionization), m/z 345 (M+1)$^+$. Slow recrystallization of 10 from hexanes affored crystals suitable for X-ray crystallographic analysis.

(−)-(1R,4aS,8aS)-1β,2β,4β,-Trimethyl-1α[(2',5'-dimethoxyphenyl)methyl]-5-exo-methylene-(3H)-1, 4,4a,5,6,7,8,8aα-octahydronaphthalene (11). To a stirred suspension of anhydrous 95% potassium tert.-butoxide (217 mg, 1.93 mmol) in 7.5 mL of benzene was added 657 mg (0.62 mmol) of methyltriphenylphosphonium bromide. The bright yellow solution was heated to reflux for 30 min. A solution of 212 mg (0.62 mmol) of ketone 10 in 3 mL of benzene was added dropwise to the heated solution of the ylide. After an additional 22 h of heating, the reaction mixture was cooled and diluted sequentially with 10 mL of ether and 3 mL of H$_2$O with rapid stirring. The layers were separated and the organic phase was washed with 2 mL of H$_2$O and 3 mL of saturated brine, and then dried (MgSO$_4$). Concentration under diminished pressure gave an almost colorless oil which was purified by chromatography on a silica gel column (10×2.5 cm). Elution with 5% EtOAc in hexanes gave 11 as colorless crystals: yield 180 mg (85%); [α]$^{25}_D$ −40.4° (c 0.5, CH$_2$Cl$_2$); mp 77–78° C.; silica gel TLC R$_f$ 0.70 (15% EtOAc in hexanes); $^1$H NMR (CDCl$_3$) δ 0.86 (s, 3H), 1.01 (d, 3H, J=5.5 Hz), 1.07 (s, 3H), 1.15–1.65 (m, 7H), 1.70–1.95 (m, 2H), 2.05–2.15 (m, 2H), 2.20–2.45 (m,1H), 2.64 (AB q, 2H, J=14 Hz), 3.72 (s, 3H), 3.75 (s, 3H), 4.33–4.47 (m, 2H) and 6.65–6.77 (m, 3H). Anal Calcd for C$_{23}$H$_{34}$O$_2$: C, 80.65; H, 10.00. Found: C, 80.82; H, 10.04.

(+)-Avarol Dimethyl Ether (12). A mixture of olefin 11 (108.5 mg, 0.317 mmol) and rhodium trichloride hydrate (16.7 mg, 0.06 mmol, 20 mol %) in 11 mL of absolute EtOH was heated to reflux. After 20 h of heating the reaction mixture was cooled and then quenched by the addition of 5 mL of H$_2$O. The aqueous phase was extracted with three 10-mL portions of CH$_2$Cl$_2$ and the combined extract was dried (MgSO$_4$) and concentrated to afford a slightly colored oil. Filtration of the residue through a plug of silica gel (10% EtOAc in hexanes) and subsequent concentration provided 12 as a clear, colorless oil which slowly solidified under high vacuum; yield 100 mg (92%); [α]$^{25}_D$ +8.88° (c 0.18, CH$_2$Cl$_2$); mp 63–68° C., lit mp ((±-12) 72–73±C, Sarma et al. J. Org. Chem. 47:1727 (1982) lit mp (natural product derivative) 80–81° C.; Minale et al., Tetrahedron Letters, 38:3401 (1974); silica gel TLC R$_f$ 0.71 (15% EtOAc in hexanes), 0.37 (5% EtOAc in hexanes); $^1$H NMR (CDCl$_3$) δ 0.75–1.15 (m, 4H), 0.87 (s, 3H), 1.01 (s, 3H), 1.24–1.65 (m, 9H), 2.0–2.15 (br m, 3H), 2.70 (br s, 2H), 3.72 (s, 3H), 3.75 (s, 3H), 5.15 (br s, 1H) and 6.65–6.85 (m, 3H); mass spectrum (chemical ionization, negative ion), m/z 341 (M−1)$^−$.

Avarone (2). In a typical procedure a stirred solution of dimethyl ether 12 (70.0 mg, 0.204 mmol) in 3.5 mL of THF was treated dropwise with a solution of 448 mg (0.82 mmol) of ceric ammonium nitrate in 3.5 mL of H$_2$O. After 15 min, the reaction mixture was diluted sequentially with 3 mL of saturated brine and 10 mL of ethyl ether. The layers were separated and the aqueous phase was subjected to additional extraction with three 10-mL portions of ether. The combined organic extract was dried (Na$_2$SO$_4$) and concentrated to afford an orange oil, which was purified by chromatography on a silica gel column (15×2 cm); elution with 5% EtOAc in hexanes provided 2 as a yellow oil; yield 25 mg (40%): [α]$^{25}_D$+21° (c 0.02, CH$_2$Cl$_2$); silica gel TLC R$_f$ 0.55 (15% EtOAc in hexanes); λ$_{max}$ (CH$_3$OH) 292 nm; $^1$H NMR (CDCl$_3$) δ 0.80–2.15 (m, 5H), 0.85 (s, 3H), 0.93 (d, 3H, J=6.5 Hz), 1.00 (s, 3H), 1.53 (br s, 1H), 2.45–2.67 (AB q, 2H, J=13.5 Hz), 5.14 (br s, 1H), 6.51 (br s, 1H) and 6.71 (m, 2H); mass spectrum (chemical ionization) m/z 312 (M+1)$^+$; mass spectrum (electron impact), m/z 311.199 (C$_{21}$H$_{27}$O$_2$ requires 311.201).

(+)-Avarol (1). In a typical procedure 25 mg (0.08 mmol) of avarone (2) was dissolved in 2 mL of ethyl ether and the resulting solution was stirred vigorously and treated dropwise with a solution containing 56 mg (0.32 mol) of Na$_2$S$_2$O$_4$ in 2 mL of H$_2$O. After 45 min., the reaction mixture was diluted with 2 mL of saturated brine followed by 10 mL of ethyl ether. The layers were separated and the aqueous phase was extracted further with three 10-mL portions of ethyl ether. The combined ether extract was dried (Na$_2$SO$_4$) and concentrated to afford an oily residue, which was purified by chromatography on a silica gel column (18×1 cm); elution with 15% EtOAc in hexanes affored (+)avarol (1) as a clear, colorless oil which solidified under vacuum as colorless needles: yield 23 mg (92%); (+)-1: [α]$^{25}_D$ +22.0° (c 1.35, CDCl$_3$); (−)-1: [α]$^{25}_D$ −19.5° (c 1.0, CKCl$_3$); mp 125–127 ° C., lit$^6$ mp (natural product) 148–150° C., lit$^5$ mp ((±−1 180–181° C.; ;silica gel TLC R$_f$ 0.10 (15% EtOAc in hexanes); λ$_{max}$ (DMSO) 305 nm; $^1$H NMR (CDCl$_3$) δ 0.86 (s, 3H), 0.99 (d, 3H, J=8 Hz), 1.02 (s, 3H), 1.51 (br s, 3H), 1.2–1.65 (m, 7H), 1.9–2.15 (m, 3H), 2.54–2.70 (AB q, 2H, J=14 HZ), 4.38 (br s, 1H), 4.41 (br s, 1H), 5.14 (br s, 1H) and 6.59 (m, 3H); mass spectrum (chemical ionization), m/z 315 (M+1)$^+$, mass spectrum (electron impact), m/z 314.225 (M)$^+$ (C$_{21}$H$_{30}$O$_2$ requires 314.225).

Optical rotation values to specific intermediates were obtained.

| | |
|---|---|
| (−)7 [α]$_D^{25}$ ......... | −121.1 (c 1.10, CH$_2$Cl$_2$) |
| (−)8 [α]$_D^{25}$ ......... | −21.6 (c 1.17, CH$_2$Cl$_2$) |
| (−)9 [α]$_D$ ........... | −115.1 (c 0.65, CH$_2$Cl$_2$) |
| (+)10 [α]$_D$ .......... | +40.0 (c 0.31, CH$_2$Cl$_2$) |
| (+)11 [α]$_D$ .......... | +41.3 (c 0.48, CH$_2$Cl$_2$) |
| (−)12 [α]$_D$ .......... | −8.75 (c 0.18, CH$_2$Cl$_8$) |

Figure 2:
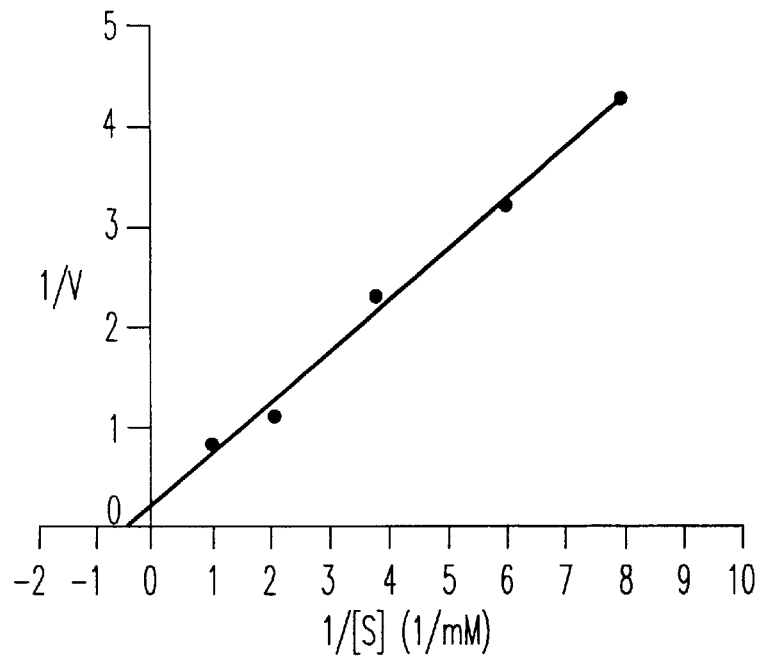
FIGS. 2–4 are reciprocal plots reflecting steady-state kinetics of the hydrolysis of various enzyme substrates.
Figure 3:
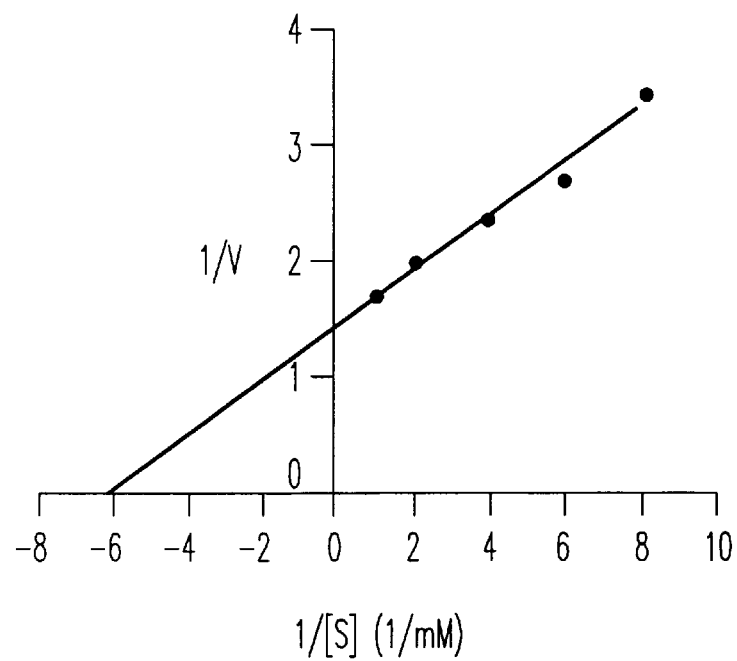
Figure 4:
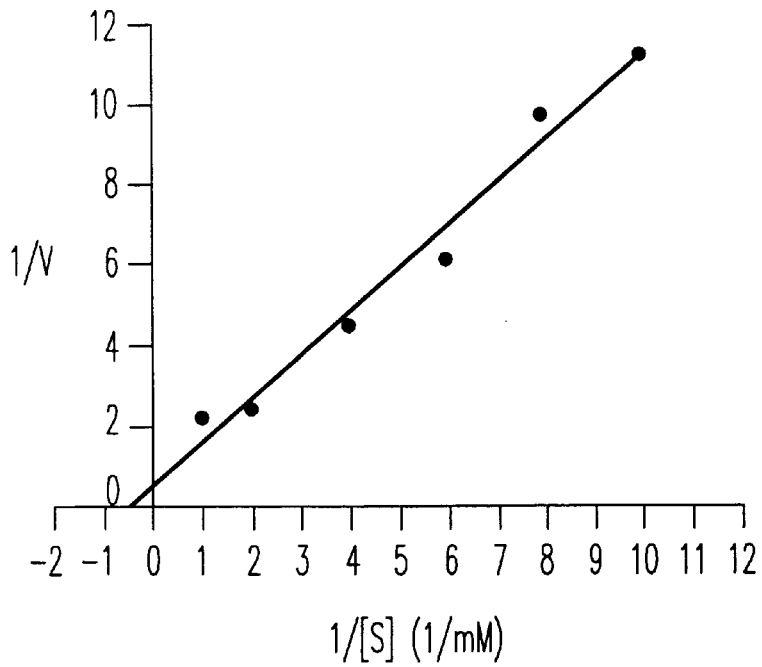

Optically pure enantiomers of avarol were synthetically prepared. A survey of potential inhibitory activity by avarol against twelve glycosidases was performed according to general procedures$^{15}$ (see experimental section). The enzymes tested and their biological sources are listed in Table 1 along with any pertinent references found for a given enzyme. In order to determine a working range for enzyme and substrate concentrations in which the rate of product formation was linear and steady-state kinetics were applicable, initial rate studies with varying substrate concentrations were performed in the absence of inhibitor. The results of these experiments for three of the enzymes studies are shown in FIGS. 2, 3 and 4. The Michaelis constants ($K_m$'s) and $V_{max}$ values for these enzymes were determined from these plots using standard graphical analysis procedures as described in ref. 17 and are summarized in Table 2.

Figure 5:
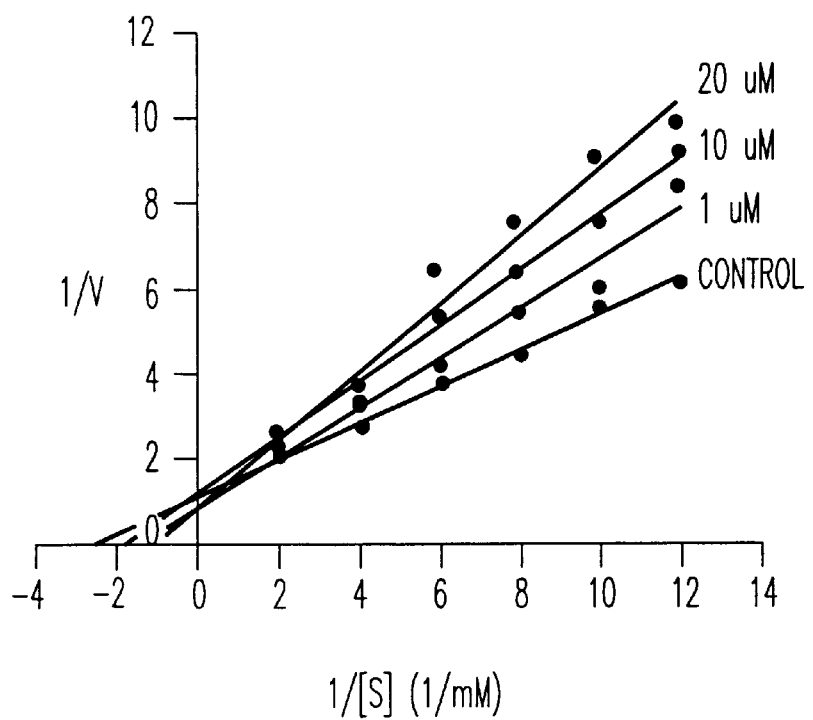
FIGS. 5 and 6 are Lineweaver-Burk reciprocal plot analyses of inhibition of hydrolysis by α-glucosidase by the enantiomers of the invention.

Initial screening assays with the enantiomeric avarols indicated significant activity by these compounds against only two of the twelve enzymes studies. Selective inhibition of α-glucosidase (Type IV, brewer's yeast, EC 3.2.1.20) and α-mannosidase hack bean, EC 3.2.1.24) was observed with virtually no inhibitory activity against the other enzymes assayed (Table 3). Interestingly, the unnatural isomer (–)-avarol was significantly more active than the naturally-occurring enantiomer in both cases. This may reflect a better diastereotopic match with respect to the enzyme-inhibitor complex for (–)-avarol versus (+)-avarol Lineweaver-Burk analyses[16] of the inhibition of α-glucosidase (brewer's yeast) by each enantiomer of synthetic avarol are shown graphically in FIGS. 4 and 5. In each case, varying the amount of inhibitor caused an increase in $K_m$ while $V_{max}$ remained unchanged, and in general, a much higher concentration of substrate in the presence of inhibitor was required to attain any given fraction of $V_{max}$ in the absence of inhibitor. These results are indicative of competitive inhibition[17] in which the substrate and inhibitor are mutually exclusive in their binding to the enzyme. This can occur when the two species compete for the same site or nearby sites on the enzyme. The equilibria that describe competitive inhibition are shown below.

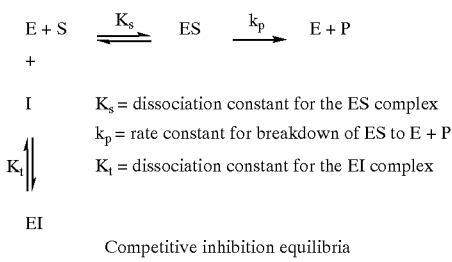

Figure 6:
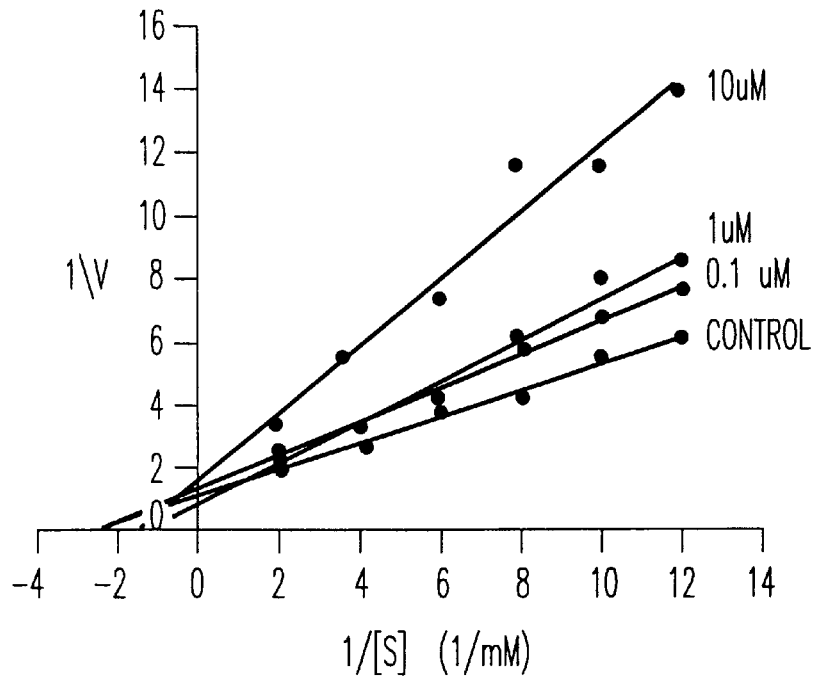
Figure 7:
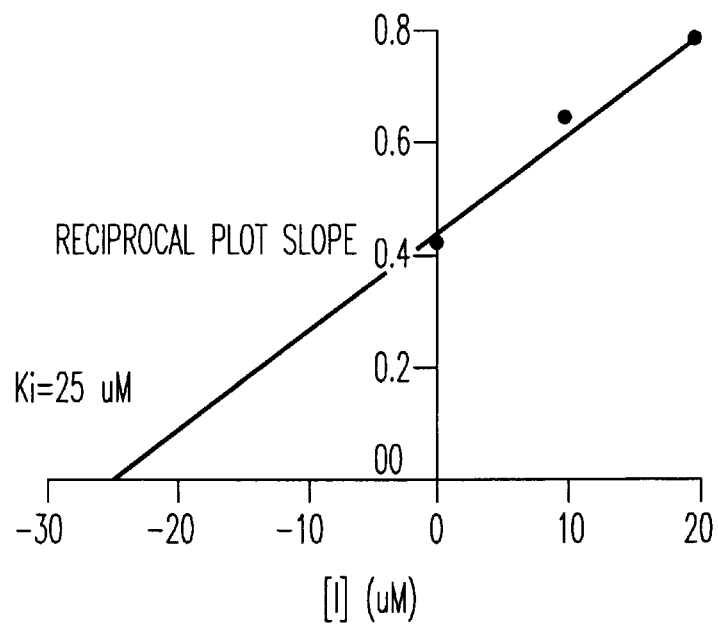
FIGS. 7 and 8 are replots of the slopes obtained for the lines in FIGS. 5 and 6.

$K_s$ = dissociation constant for the ES complex
$k_p$ = rate constant for breakdown of ES to E + P
$K_I$ = dissociation constant for the EI complex Competitive inhibition equilibria A replot of the slopes obtained for each line in the Lineweaver-Burk plot versus the corresponding inhibitor concentration (FIGS. 6 and 7) and subsequent linear extrapolation gave $K_i$=25 μM for (+)-avarol and $K_i$=9.5 μM for (–)-avarol. The fact that the points in these plots appear to be non-linear suggests that the inhibition may be of the partial competitive-type.[18] This situation arises when the substrate and inhibitor bind the enzyme at different sites with the substrate having a greater affinity for the free enzyme and both the ES and the ESI complex yield product with equal facility. The equilibria describing this phenomenon are shown below.

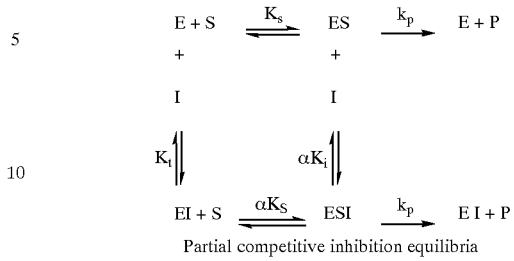

Partial competitive inhibition equilibria

The α factor represents the amount by which $K_S$ changes when I binds to the enzyme. The overall equilibrium constant for the formation of ESI remains the same regardless of which path was taken in its formation. Since the ES and ESI complexes are equally efficient in producing product, $V_{max}$ remains unchanged and $K_m$ is increased in the presence of inhibitor. These results are analogous to pure competitive inhibition, the difference only becoming apparent when replots are performed as described above.

Selective inhibition of glycosidase enzymes was also demonstrated in these trials for the natural product ilimaquinone. Steroisomerism should provide similar enhanced selectivity. Ilimaquinone was demonstrated to inhibit α-glucosidase (20% inhibition at 20 μM and shown to be a strong inhibitor of amyloglucosidase (Table 3)).

Figure 8:
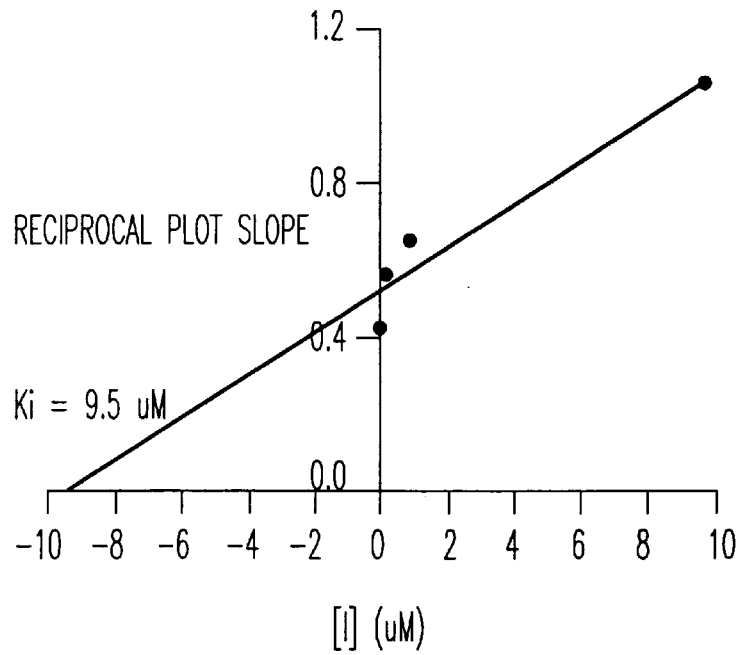

In separate experiments, the concentrations required for 50% inhibition of enzymatic activity ($IC_{50}$'s) were determined for the enantiomeric avarols against α-D-glucosidase (brewer's yeast) and the results are shown graphically in FIG. 8. An $IC_{50}$ of 7.6 μM was calculated for unnatural (–)-avarol and the value for the natural (+)-isomer was greater than 20 μM.

Figure 9:
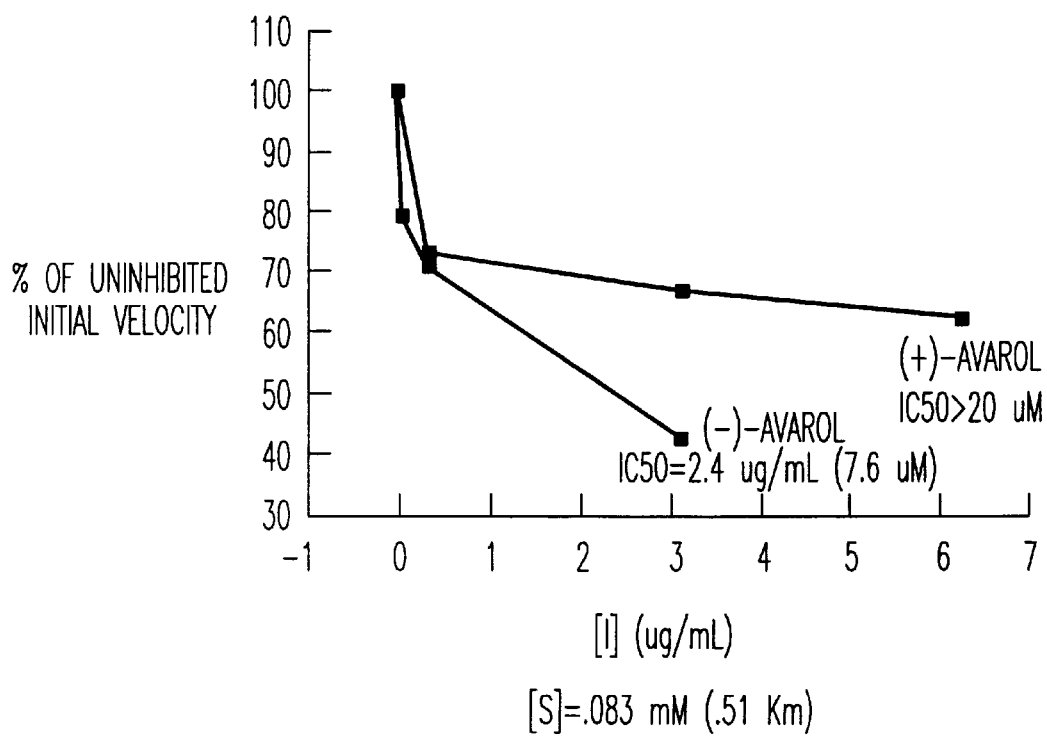
FIGS. 9 and 10 are plots of enzyme activity as a function of varying concentrations of the enantiomers of avarol.
Figure 10:
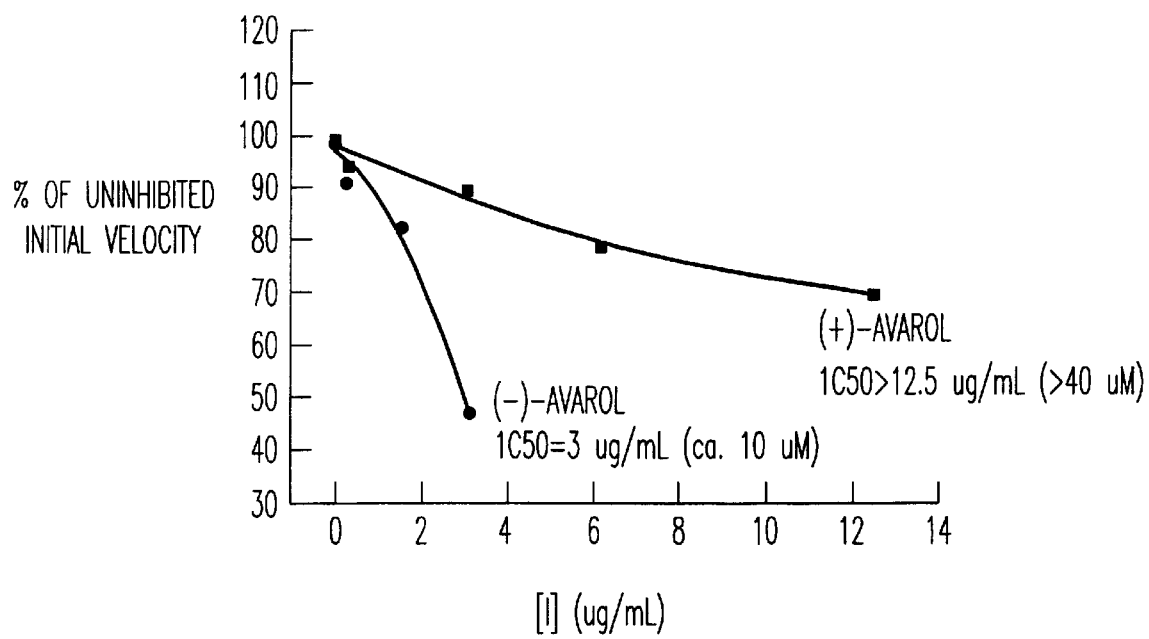

Enzymatic assays with a α-D-mannosidase (jack bean) were complicated by the higher $K_m$ of the enzyme (2.04 mM) requiring higher substrate concentrations and the relative insolubility of the ρ-nitrophenyl mannoside substrate in aqueous media. The assay had to be performed using hot solutions of the substrate which were pipetted with some expected difficulty. Nonetheless, $IC_{50}$ values of >40 μM and ~10 μM were obtained for the (+)- and (–)-enantiomers of avarol respectively. These results are depicted graphically in FIG. 9.

The remarkable selective inhibition of glycosyl hydrolases exhibited by avarol and ilimaquinone is intriguing as the chemical structures of these sesquiterpenes differ drastically from the structures of known inhibitors of this class of enzymes. The latter are generally characterized as transition-state analogs of the putative carbohydrate oxonium ions intermediate to the hydrolyzed products in these enzymatic reactions. This research constitutes the first enantioselective total synthesis of avarol and its optical antipode and presents avarol (1) as a novel glycosidase inhibitor with remarkably high enzyme selectivity. Furthermore, the magnitude of the inhibitory activity is dependent on the absolute configuration of the inhibitor as the unnatural isomer is the more potent inhibitor of these key enzymes.

Importantly, the magnitude of inihibition of α-glucosidase (yeast) by avarol is comparable to that exhibited by deoxynojirimycin ($K_i$=23 μM, yeast α-glucosidase) and castanospermine derivative ($K_i$=1.27 μM, cellular α-glucosidase I) which are curently under investigation as potential anti-HIV drugs. It is interesting to note that Muller et al., U.S. Pat. No. 4,939,177 have described pharmaceutical compositions and the potential use of the natural isomers of avarol, U.S. Pat. No. 4,946,869 and avarone U.S. Pat. No. 5,026,732 as agents for the control of AIDS and AIDS-Related Complex. These patents also describe the biological activity of several synthetic avarol and avarone analogs. The present findings lend further credence to the potential use of avarol and congeners as anti-HIV agents. Additionally, new potent anti-HIV agents may be prepared by incorporating into avarol some of the salient chemical functionality inherent to several known glycosidase inhibitors while ideally retaining the documented low toxicity of both avarol and avarone. Such chemical modifications and those aimed at exploiting the factors responsible for tight binding in the natural substrates are set forth following the Experimental Section below.

Experimental

Enzymatic Assays. Piperazine-N,N'-bix-(2-ethanesulfonic acid)(PIPES) buffer, enzymes, and substrates were purchased from Sigma and used as received. Buffer solutions and enzymes (desiccated) were stored at 4° C. p-Nitrophenyl glycoside substrates were stored desiccated at −20° C. Enzyme inhibition assays and initial rate studies were carried out with the appropriate p-nitrophenyl glycoside substrates following the general procedure of Kajimoto et al., J. Am. Chem. Soc. 113:6187 (1991) with the exception that amyloglucosidase (EC 3.2,1.3, Asp. niger) was assayed following the method of Saul et al., Arch. Biochem. Biophys. 221:593 (1983). Assays were performed in a Perkin-Elmer Lambda Array 3840 Spectrophotometer using the built-in drive method (resolution=0.25, average=8) in a quartz cuvette (1 cm pathlength). Background absorption spectra were acquired using millipore filtered water as medium. Steady-state kinetics were maintained by adjusting the amount of enzyme used in each assay so that less than 10% of the substrate was converted to product for the duration of the reaction. Reactions were monitored at 400 nm (the absorbance of the p-nitrophenol product, $\epsilon=3204.5$ $M^{-1}$ $cm^{-1}$) for a given amount of time and the initial rates were calculated and expressed as $\mu$mols p-nitrophenol formed per unit enzyme per second. Absportion readings for control reactions were corrected for the small baseline absorbance at time zero. Small discrepancies between time zero absorbance readings in a given inhibition assay and a time zero reading in a control assay were used to correct the overall absorbance change calculated in the inhibition assay. Inhibitors were dissolved in uv-grade absolute methanol. All control and inhibition assay mixtures contained methanol as cosolvent (2% v/v fmal concentration) which did not significantly affect the activity of the enzymes in any of the assays.

Typical assay: A 1.5-mL quartz cuvette was charged with 940 $\mu$L of PIPES-NaOAc buffer solution (pH 6.56), 20 $\mu$L of inhibitor solution, and 20 $\mu$L of enzyme solution. The result was mixed well and then equilibrated at 37° C. for two minutes. 20 $\mu$L of the appropriate p-nitrophenyl glycoside solution was then added to initiate the reaction with rapid mixing. The reaction was monitored at 400 nm for 1 min and the absorbance change was used to calculate the initial hydrolysis rate. Lineweaver-Burk plots were constructed by repeating this procedure with varying substrate and inhibitor concentrations.

Figure 11A:
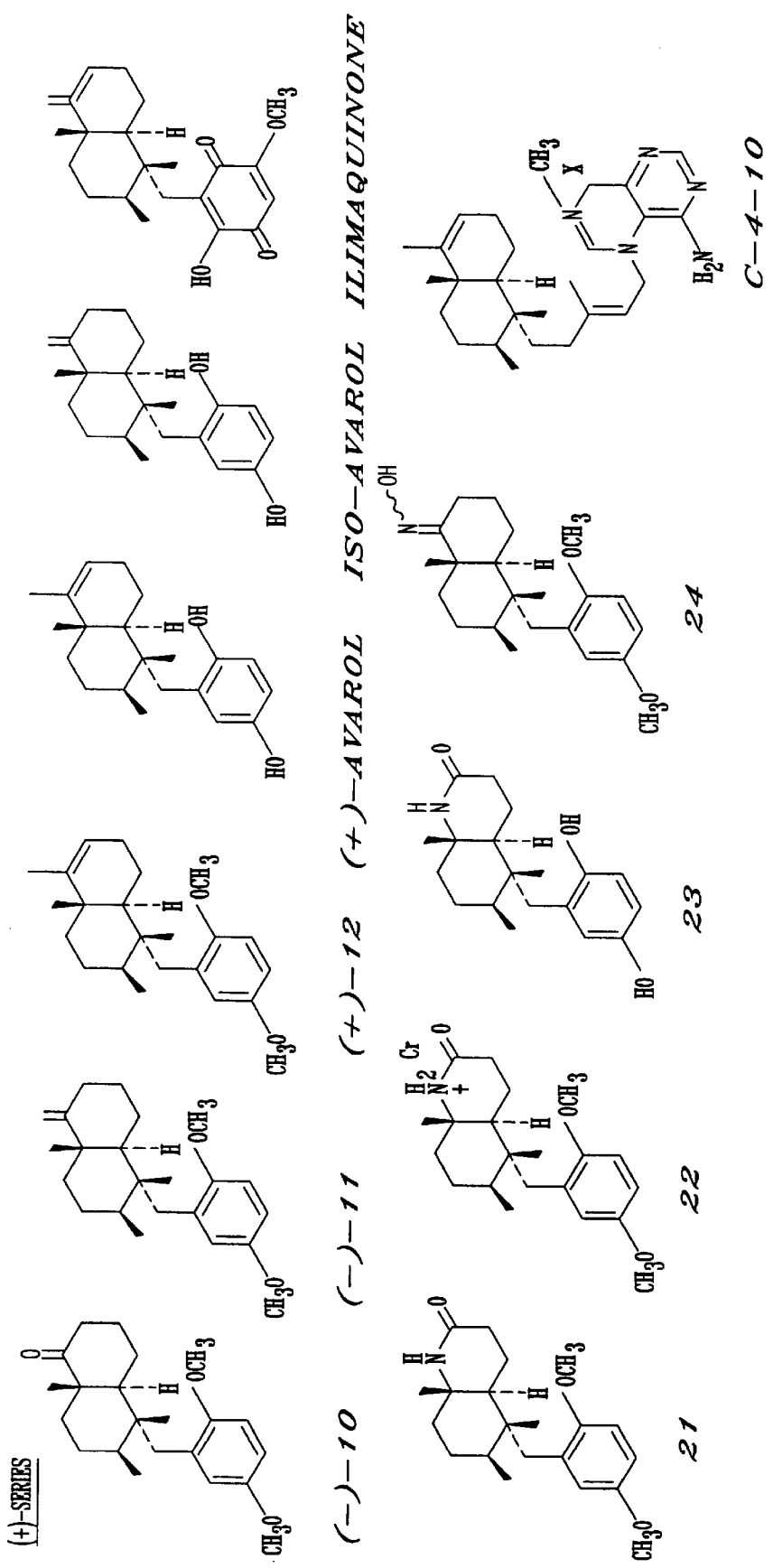
FIG. 11 sets forth the structural formulae of compounds synthesized as potential enzyme inhibitors pursuant to this invention.
Figure 11B:
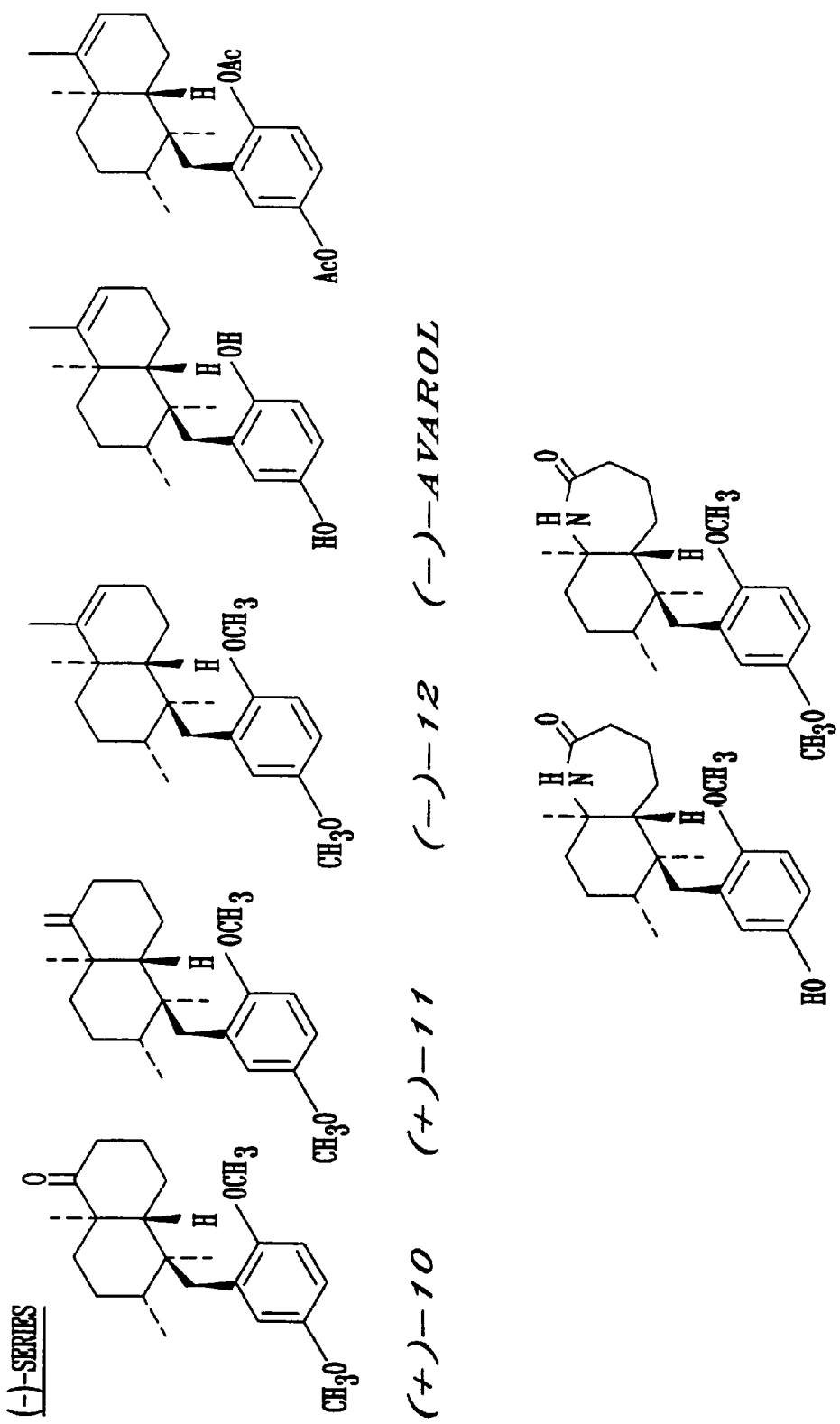

Results of this testing led to the synthesis of additional potential inhibitors, all according to the general scheme embodied in FIG. 1, allowing for different substituent identities. These compounds, both (+) and (−) enantiomers, are set forth in structural formula in FIG. 11. This work forms the basis for those classes of inhibitors, by structure.

Inhibitors By Structure

As depicted in FIG. 12, there are three basic structural motifs (A,B,C,) which represent the types of compounds useful in this invention as inhibitors of the hydrolase activity of glycosidase enzymes on a substrate. In this application, lower alkyl refers to alkyls of 1–12 carbon atoms, and aryl refers to phenyl and naphthyl. Substituted aryl is phenyl or naphthyl with 1–4 substituents of lower alkyl OH, lower alkoxy, amine or amide identity. Motif A retains the double bond functionality, B replaces the double bond with a heteroatom (O,N.S) at either of its ends, and C contains a highly reactive cyclopropyl ring in its place. The A, B, and C motifs are based on the structures of known inhibitors of glycosidases, namely avarol, iminosugars e.g., (1-deoxynojirimycin, N-butyl-1-deoxynojirimycin, castanospermine and 6-O-butanoyl-castanospermine), and conduritol epoxides respectively.

Examination of energy minimized molecular models of avarol and the putative oxonium ion implicated as a transitional structure in the glycosidase hydrolysis mechanism shows an uncanny similarity in the structures of these two species (see insert below).

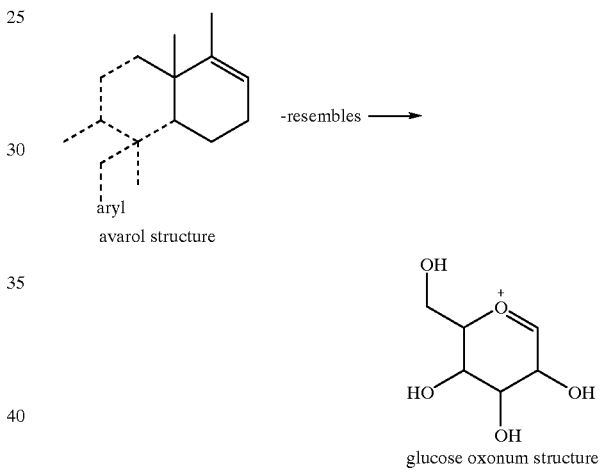

avarol structure glucose oxonum structure

Computer-assisted molecular modeling showing natural and unnatural avarol (ball and stick structures) overlayed with the D-glucose oxonium ion (darker tubular structure) is set forth in FIG. 13A and B. Consistent with the inhibition data acquired, these models show a greater resemblance of unnatural (−)-avarol to the oxonium ion structure. Thus, the origin of inhibition activity for these compounds may be their ability to structurally mimic the natural substrates of glycosidase enzymes.

Considering motif A, placement of conjugate acceptors ($CO_2$alkyl, CHO, $NO_2$, etc.) at $R_1$ or $R_2$ serve to activate the double bond to react with nucleophiles in the active site of the enzyme. Halogens (Br, Cl, F etc.) at the position corresponding to $R_2$ of certain sugar derivatives have provided very potent inhibitors.

In motif B, a heteroatom such as nitrogen is incorporated at position X or Y, and in doing so, transforms the avarol structure into a hybrid compound to exploit the features of known inhibitors such as deoxynojirimycin.

Motif C embodies the design of potential suicide substrates or irreversible inhibitors. These highly reactive compounds should react readily within the active site of the enzyme resulting in permanent deactivation of its activity.

Such compounds are very useful as mechanistic probes, and also possess medicinal potential provided the selectivity of their biological activity is retained.

In all three motifs, the incorporation of a functionality capable of hydrogen bonding (OH, NH, SH, etc.) can reasonably be expected to increase the binding energy, selectivity, and overall activity of these analogs. Furthermore, at positions $R_2$, $R_3$, $R_8$ and $R_9$, glucose residues linked to the avarol nucleus through different hydroxyl groups are employed. These choices for modification are intended to mimic the actual biological substrates (amylose and maltose) that these enzymes target in the cell. The structure of the naturally-occurring α-glucosidase inhibitor, acarbose, is supportive of this type of modification. At least one free hydroxyl group on the aryl moiety is needed for activity. Other groups capable of hydrogen bonding ($NH_2$, SH, etc.) strategically placed on the aryl moiety and placement of the aryl moiety at different positions on the avarol nucleus should also render the molecule active. We expect avarone and other quinone congeners to exhibit activity in light of their reported ability to covalently modify biological enzymes in cells.

The other indicated modifications are selected to (i) match the steric boundaries of the active site of these enzymes through a straightforward medicinal chemistry approach, and (ii) render the molecule more substrate-like.

TABLE 1

Enzymes assayed and their biological sources

| Enzyme | Source | Ref |
|---|---|---|
| β-glucosidase (EC 3.2.1.21) | almonds | 29 |
| α-glucosidase (EC 3.2.1.20, type IV) | brewer's yeast | 30 |
| α-mannosidase (EC 3.2.1.24) | jack beans | 31 |
| β-N-acetylglucosaminidase (EC 3.2.1.30) | bovine kidney | 32 |
| β-galactosidase (EC 3.2.1.23, grade XI) | *Aspergillus oryzae* | |
| β-galactosidase (EC 3.2.1.23) | *Aspergillus niger* | |
| α-L-fucosidase (EC 3.2.1.51) | bovine kidney | |
| α-galactosidase (EC 3.2.1.22) | *Escherichia coli* | |
| α-galactosidase (EC 3.2.1.22) | green coffee beans | |
| amyloglucosidase (EC 3.2.1.3) | *Aspergillus niger* | 33 |
| β-mannosidase (EC 3.2.1.25) | snail | |
| β-xylosidase (EC 3.2.1.37) | *Aspergillus niger* | |

TABLE 2

Kinetic parameters derived from initial rate experiments (FIGS. 1, 2, and 3)

| Enzyme | $K_m$ (mM) | $V_{max}$ (μmols product/unit enzyme/sec) |
|---|---|---|
| β-glucosidase | 2.03 | 40.3 |
| α-glucosidase | 0.16 | 6.86 |
| α-mannosidase | 2.04 | 19.2 |

TABLE 3

Results of initial screening assays for enzyme inhibition

| | % Enzyme activity relative to control[a] in the presence of | | | |
|---|---|---|---|---|
| Enzyme | (+)-1 | (−)-1 | 20 μM ilimaquinone | 20 μM C-4-10 |
| β-glucosidase | 102 (20 μM) | 96 (20 μM) | nd[b] | nd |
| α-glucosidase | 63 (10 μM) | 43 (10 μM) | 82 | nd |
| α--mannosidase | 90 (10 μM) | 47 (10 μM) | nd | nd |
| β-N-acetylglucosaminidase | 102 (20 μM) | 89 (10 μM) | 96 | 91 |
| β-galactosidase (*Asp. oryzae*) | 100 (40 μM) | 99 (20 μM) | 98 | 108 |
| β-galactosidase (*Asp. niger*) | 104 (40 μM) | 111 (20 μM) | 111 | 95 |
| α-L-fucosidase | 101 (40 μM) | 108 (20 μM) | 109 | 100 |
| α-galactosidase (*E. coli*) | 90 (40 μM) | 94 (20 μM) | 101 | 102 |
| α-galactosidase (green coffee beans) | 82 (40 μM) | 83 (20 μM) | 97 | 96 |
| amyloglucosidase | 113 (40 μM) | 94 (20 μM) | 57 | 94 |
| β-mannosidase | 106 (40 μM) | 101 (20 μM) | 108 | 109 |
| β-xylosidase | 100 (40 μM) | 91 (20 μM) | 105 | 102 |

[a]Control experiments were run in the presence of 2% MeOH (final volume) in the absence of inhibitor.
[b]nd = not determined.

Literature Citations (1) O'Brien, P. J. Chem-Biol Interactions 1991, 80, 1–41 and references therein.
(2) Ref. 1 and (a) Muller, W. E. G.; Maidhof, A.; Zahn, R. K.; Schroder, H. C.; Gasic M. J.; Heidemann, D.; Bernd, A.; Kurelec, B.; Eich, E.; Seibert, G. Cancer Res. 1985, 45, 4822. (b) Cozzolino, R.; De Giulio, A.; De Rosa, S.; Strazzullo, G. J. Nat. Prod. 1990 53, 699.
(3) (a)Sinnott, M. Chem. Rev. 1990, 90, 1171–1202. (b) Elbein, A. D. Annu. Rev. Biochem. 1987, 56, 497.
(4) Koshland, D. E. Biol. Rev. 1953, 28, 416.
(5) Henrissat, B.; Callebaut, I.; Fabrega, S.; Lehn, P.; Mornon, J-P.; Davies, G. Proc. Natl. Acad, Sci. USA 1995, 92, 7090.
(6) (a) Gruters, R.; Neefjes, J. J.; Tersmette, M.; de Gode, R.; Tulp, A.; Huisman, H. G.; Miedema, F.; Plogh, H. L. Nature 1987, 330, 74. (b) Walker, B. D.; Kowalski, M.; Goh, W. C.; Kozarsky, K.; Kriger, M.; Rosen, C.; Rohrschneider, L.; Haseltine, W. A.; Sodroski, J. Proc. Natl. Acad, Sci. USA 1987, 84, 8120.
(7) Leonhardt, W.; Hanefield, M.; Fischer, S.; Schulze, J. Eur. J. Clin. Invest. 1994, 24, Suppl. 3,45.
(8) Humphries, M. J.; Matsumoto, K.; White, S. L.; Olden, K. Cancer Res. 1986, 46, 5215.
(9) Locke, E. P.; Hecht, S. M. Chem. Commun. 2717 (1996).
(10) (a) Minale, L.; Riccio, R.; Sodano, G. Tetrahedron Lett. 1974, 3401. (b) Rosa, S.; Minale. L.; Riccio, R.; Sodano, G. J. Chem. Soc. Perk. Trans. 1 1976, 1408.
(11) Muller, W. E. G.; Dogovic, N.; Zahn, R. K.; Maidhof, A.; Diehl-Seifert, B.; Becker, C.; Sachsse, W.; Gasie, M. J.; Schroder, H. C. Bas. Appl. Histrochem. 1985, 29, 321–330.
(12) Sarin, P. S.; Sun, D.; Thronton, A.; Muller, W. E. G. J. nat'l Cancer Inst. 1987, 78(4), 663.

(13) Kurelec, B.; Zahn, R. K.; Gasic, M. J.;Britvic, S.; Lucic, D.; Muller, W. E. G. Mutation Res. 1985, 144, 63–66.
(14) Maron, D. M.; Ames, B. N. Mutation Res. 1983, 113, 173.
(15) (a) Kajimoto, T.; Liu-K.-C.; Pederson, R. L.; Zhong, Z.; Ichikawa, Y.; Porco, J. A.; Wong, C.-H. J. Am. Chem. Soc. 1991, 113, 6187–6196. (b) Saul, R.; Chambers, J. P.; Molyneux, R. J.; Elbein, A.d. Arch. Biochem. Biophys. 1983, 221, 593.
(16) Lineweaver, H.; Burke, D. J. Am. Chem. Soc. 1934, 58, 658.
(17) Segel, I. H. IN Enzyme Kinetics; Wiley-Interscience: New York, 1993; Ch. 3.
(18) Segel, I. H. In Enzyme Kinetics; Wiley-Interscience: New York, 1993; Ch. 4.
(19) Luibrand, R. T.; Erdman, T. R.; Vollmer, J. J.; Scheuer, P. J.; Finer, J.; Clardy, J. Tetrahedron 1979, 35, 609.
(20) This compound was isolated and characterized by Dr. Jie Chen in these laboratories.
(21) (a) Winchester, B.; Fleet, G. W. J. Glycobiology 1992, 2(3), 199–210. (b) Winkler, D. A.; Holan, G. J. Med. Chem. 1989, 32, 2084–2089.
(22) Ref. 3 and 21b.
(23) Ref. 9.
(24) (a) Brougham, P.; Cooper, M. S.; Cummerson, D. A.; Heaney, H.; Thompson, N. Synthesis 1987, 1015. (b) Heaner Aldrichimica Acta 1993, 26(2), 35–45.
(25) Pochini, A.; Puglic, G.; Ungaro, R. Synthesis 1983, 906.
(26) (a) Katada, T.; Eguchi, S.; Esaki, T.; Sasaki, T. J. Chem. Soc. Perk. Trans. 1 1984, 2649. (b) Balasubramanian, K. K.; Selvaraj, S. J. Org. Chem. 1980, 45, 3726. (c) Chauhan, M. S.; Dean, F. M.; Matkin, D.; Robinson, M. L. J. Chem. Soc. Perk Trans 1 1973, 120.
(27) Smith, A. B.; Mewshaw, R. J. Org. Chem. 1984, 49, 3685.
(28) Ref. 9.
(29) Dale, M. P.; Ensley, H. E.; Kern, K.; Sastry, K. A. R.; Byers, L. D. Biochemistry 1985, 24(14), 3530.
(30) Truscheit, E.; Frommer, W.; unge, B.; Muller, L.; Schmidt, D. D.; Wingender, W. Angew, Chem. Int. Ed. Eng. 1981, 20, 744–761.
(31) Li-Y.-T. J. Biol. Chem. 1967, 242(23), 5474.
(32) (a) Li, S.-C.; Li, Y.-T. J. Biol. Chem. 1970, 245(19), 5153. (b) Bahl, O. P.; Agrawal, K. M. L. J. Biol. Chem. 1969, 244(11), 2970–2978.
(33) Frandsen, T. P.; Christensen, T.; Stoffer, B.; Lehmbeck, J.; Dupont, C.; Honzatko, R. B.; Svensson, B. Biochemistry 1995, 34, 10162–10169.

What is claimed is:

1. (−)-avarol.
2. The compound of claim 1, wherein said compound is optically pure.
3. A method of inhibiting the hydrolase activity of a glycosidase enzyme on a substrate therefore, comprising combining, with said enzyme and said substrate, a compound of the structural formula A, B or C

A

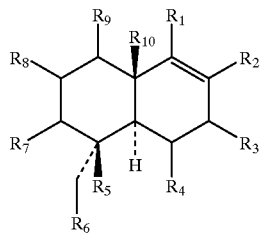

B

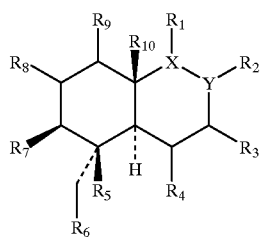

C

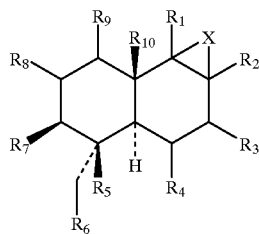

X = C, O, N, S
Y = C, O, N, S
$R_1$ = H, lower alkyl, $CO_2$alkyl, CHO, $NO_2$, CN, ═X

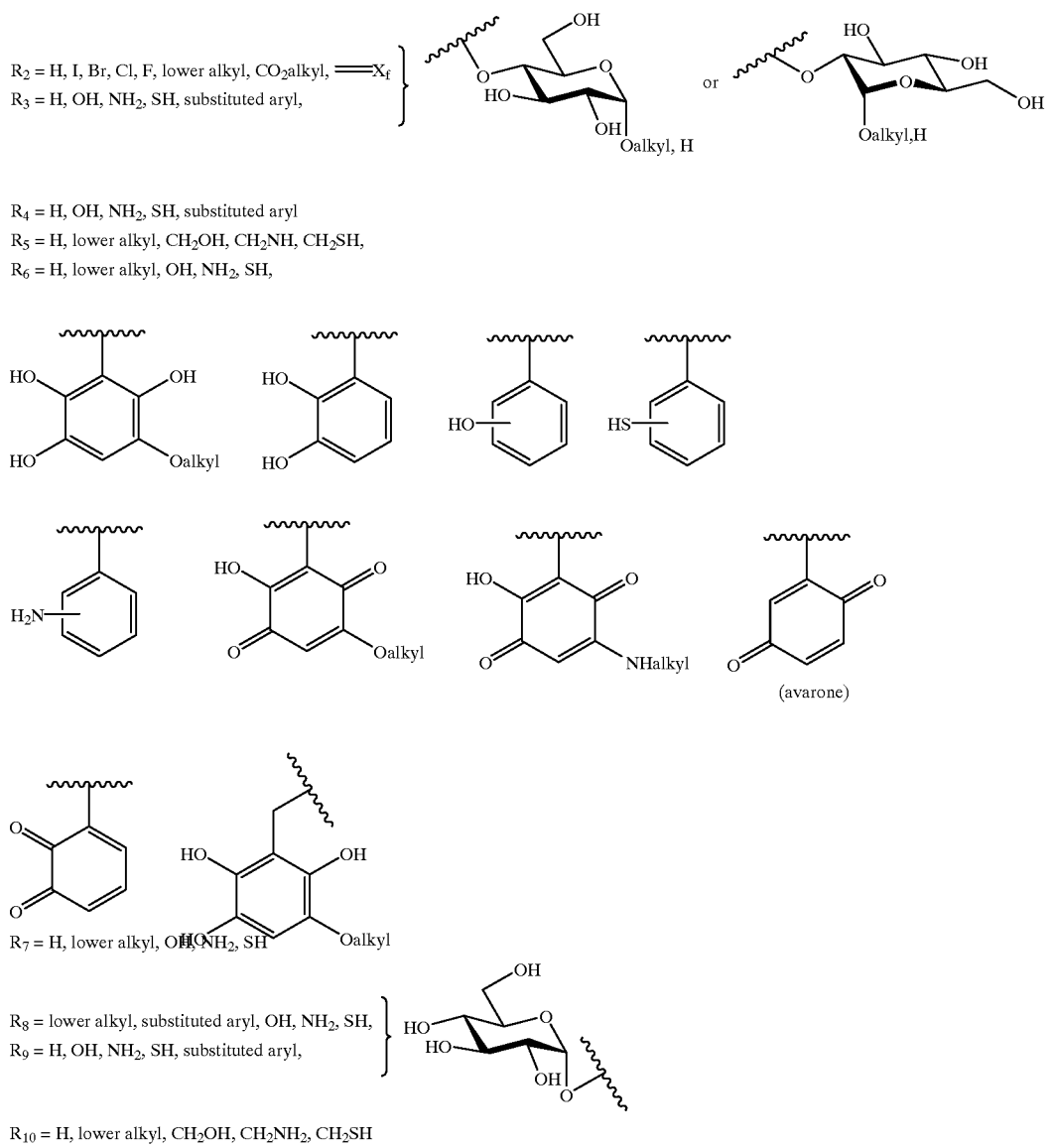

4. The method of claim 3, wherein said enzyme, substrate and said compound combined therewith are present in a biological system.

5. The method of claim 4, wherein said biological system is a mammal.

6. The method of claim 5, wherein said glycosidase is α-glucosidase or α-mannosidase.

7. The method of inhibiting the activity of α-glucosidase or α-mannosidase on a substrate therefore, comprising combining, with said enzyme and said substrate, a compound selected from the group consisting of avarol or avarone.

8. The method of claim 3, wherein said avarol is optically pure.

9. The method of claim 3, wherein said compound combined with said enzyme and said substrate is (−)-avarol.

10. The method of claim 7, wherein said enzyme, substrate and said compound combined therewith are present in a biological system.

11. The method of claim 10, wherein said biological system is a mammal.

12. A method of inhibiting the hydrolase activity of a glycosidase on a substrate therefor, comprising, combining, with said enzyme and said substrate or compound of the formula A, B or C A 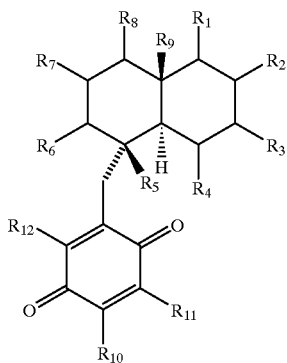

B 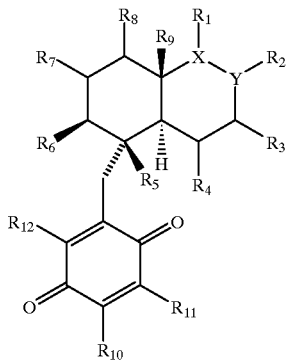

C 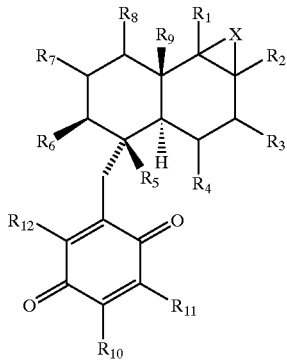

wherein
X and Y independently are C, O, N, S or
X and Y together may form a double bond $R_1$ is H, lower alkyl, CHO, $NO_2$, CN, =X $R_2$ is H, I Br, Cl, F, lower alkyl, $CO_2$lower alkyl $R_3$, $R_4$ are independently H, OH, $NH_2$, SH, substituted aryl $R_5$ is H, lower alkyl, $CH_2$, OH, $CH_2$, NH, $CH_2SH$ $R_6$, $R_7$ and $R_8$ are independently H, lower alkyl, OH, $NH_2$, SH $R_9$ and $R_{10}$ are independently H, lower alkyl, CHO, $NH_2$, $NO_2$, CN, OH and SH $R_{11}$ and $R_{12}$ are, independently, H, OH, CHO, COO, COOlower alkyl, $NH_2$, $NO_2$, NHlower alkyl or HNZ, wherein Z is an amino acid or amino acid fragment wherein any one or two of $R_2$, $R_3$, $R_7$ and $R_8$, instead of the values assigned above, may be

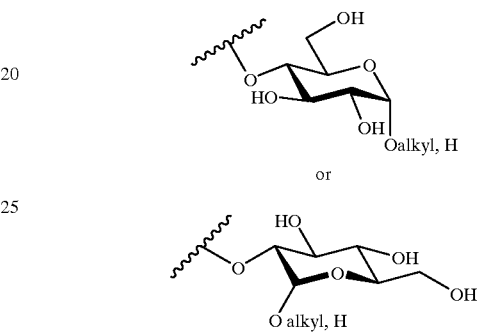

13. The method of claim 12, wherein said enzyme, substrate and said compound combined therewith are present in a biological system.

14. The method of claim 13, therein said biological system is a mammal.

15. The method of claim 14, wherein said glucosidase is α-glucosidase or amyloglucosidase.

16. A method of inhibiting the activity of α-glucosidase or amyloglucosidase on a substrate therefore, comprising combining, with said enzyme and said substrate, an inhibitory amount of ilimaquinone.

17. A method of effecting anti-tumor chemotherapy in an individual in need of same, comprising:

administering to said individual an anti-tumor chemotherapeutic amount of a compound of claim 3.

18. A mixture of (+) and (−) optical isomers of avarol or avarone.

* * * * *